United States Patent [19]
Davies et al.

[11] Patent Number: 6,043,296
[45] Date of Patent: Mar. 28, 2000

[54] TREATED GLASS POLYALKENOATE CEMENT

[75] Inventors: Edward Henry Davies, Orpington; Bipin Chandra Muljibhai Patel, Greenford; Gavin John Pearson, Ashampstead; Alan Donald Wilson, Liphook, all of United Kingdom

[73] Assignee: BTG International Limited, London, United Kingdom

[21] Appl. No.: 09/143,616

[22] Filed: Aug. 28, 1998

Related U.S. Application Data

[63] Continuation of application No. PCT/GB97/00543, Feb. 26, 1997
[60] Provisional application No. 60/020,778, Jun. 28, 1996.

[30] Foreign Application Priority Data

Feb. 29, 1996 [GB] United Kingdom .................. 9604343

[51] Int. Cl.$^7$ .............................. C08K 3/32; A61K 6/083
[52] U.S. Cl. ......................... 523/116; 524/450; 524/547; 524/556; 524/832; 528/503; 433/228.1; 106/35

[58] Field of Search ............................ 523/116; 528/503; 524/450, 556, 832, 547; 433/228.1; 106/35

[56] References Cited

U.S. PATENT DOCUMENTS

| | | | |
|---|---|---|---|
| 4,731,394 | 3/1988 | Vogel et al. | 523/116 |
| 5,422,384 | 6/1995 | Samuels et al. | 524/556 |
| 5,453,456 | 9/1995 | Mitra et al. | 523/116 |

FOREIGN PATENT DOCUMENTS

| | | | |
|---|---|---|---|
| 0 331 071 | 9/1989 | European Pat. Off. | |
| 0 386 525 | 9/1990 | European Pat. Off. | |
| 0442326 | 8/1991 | European Pat. Off. | 523/116 |
| 26 37 825 | 2/1978 | Germany . | |

*Primary Examiner*—Andrew E. C. Merriam
*Attorney, Agent, or Firm*—Nixon & Vanderhye

[57] ABSTRACT

Glass polyalkenoate (glass ionomer) cements are used formed into dental crowns, despite their reputedly inadequate toughness, strength and wear-resistance early after forming for such an application, by heating the newly formed glass ionomer crown under a relative humidity of 100% in a bomb under silicone oil at 120–200° C. for an hour.

18 Claims, 1 Drawing Sheet

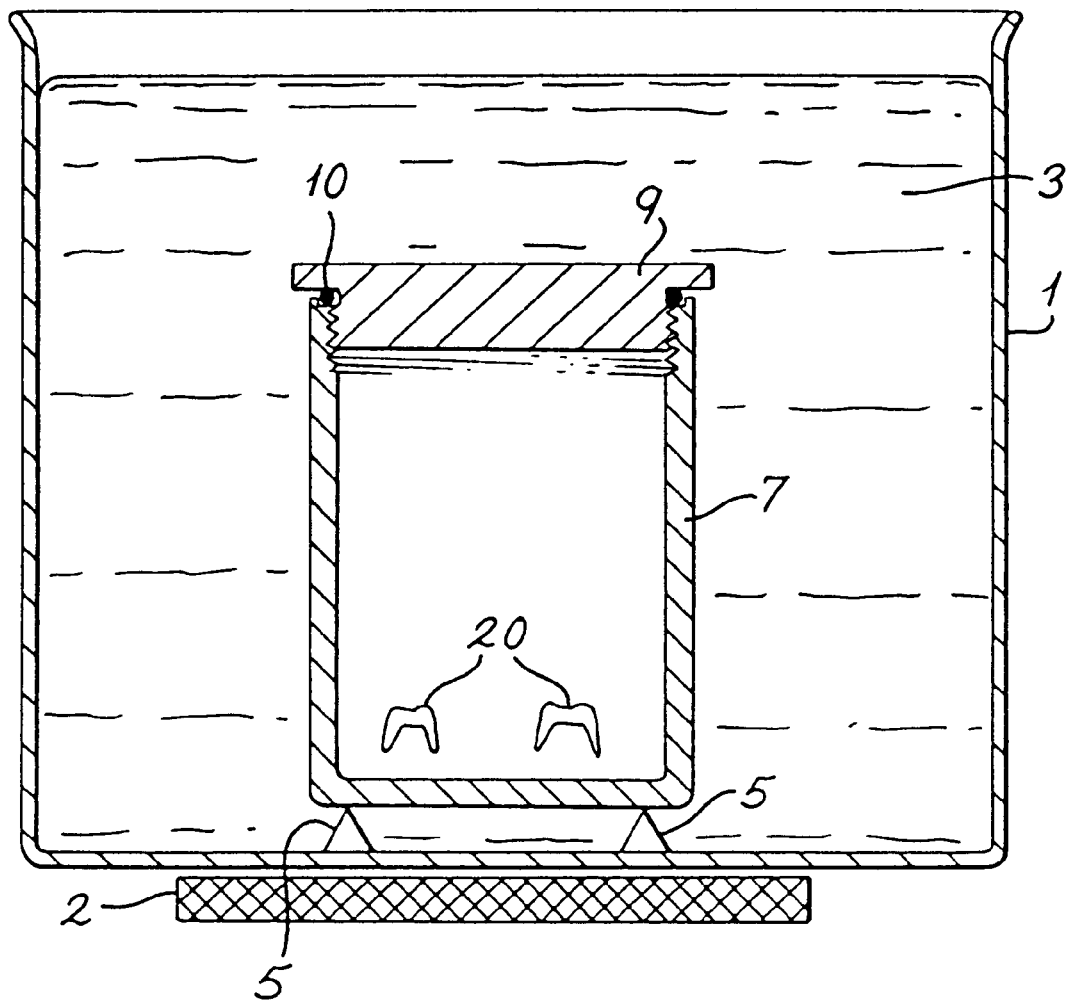

TREATED GLASS POLYALKENOATE CEMENT

This application claims benefit of provisional application Ser. No. 60/020,778 filed Jun. 28, 1996, continuation of PCT/GB97/00543 filed Feb. 26, 1997.

This invention relates to a method of treating glass ionomer cement to improve its suitability as a dental crown material, and the invention extends to the cement so treated and to dental crowns so made. Glass polyalkenoate cements are the hardened mass formed by gelation following acid-base reaction of an ion-leachable aluminosilicate glass with a polyalkenoic acid, as taught in UK Patent 1316129 and many subsequent publications, and they have become the material of choice for Class III, IV and V dental restorations. However, neither they nor any other material have so far displayed all the necessary properties to become a reliable material for a one-visit permanent dental crown.

At present, when a dental patient requires a tooth to be crowned, a lengthy procedure is involved. Impressions are taken of the patients tooth. The patient is given a temporary crown. The impressions are sent to a dental laboratory to make up a permanent ceramic crown. The patient returns to the surgery at some future date when the permanent crown is ready, and on this return visit the temporary crown is removed and the permanent one fitted.

The "two-visit" procedure is a nuisance for the patient, the use of an outside laboratory increases the expense, and often the temporary crown will either not come off when required or will have dropped off prematurely.

Glass ionomer cements would be a convenient material for making crowns in the surgery because the dental profession is already well used to handling this material and because the crown could conveniently and reliably be adhered to the prepared tooth by glass ionomer luting cement. However, glass ionomer cements develop their final strength after a considerable period, and even then have not been considered tough and wear-resistant enough to serve as crowns.

In designing a crown material, it is desirable to mimic a natural tooth as closely as possible, but this is very difficult. Tooth enamel is an extremely hard substance, whose hardness is however not matched by its wear-resistance. Also, it overlies dentine, of lesser compressive and flexural (90–100 MPa) strength. A crown whose properties deviate too much from those of natural tooth will either fail prematurely or inflict damage on the opposing dentition. A material whose flexural strength is similar to that of dental porcelain can be assumed to be regarded as acceptable.

According to the present invention, a method of treating an acid-base reaction cement (e.g. a zinc-eugenol cement or a (dental silicate plus phosphoric acid) cement or one where the base is of acid-degradable glass and wherein the cement is preferably a glass/polyphosphonate cement (e.g. with poly(vinyl phosphonic acid) or a glass polyalkenoate cement) comprises heating an at least partly set shaped glass-acid mixture to above 120° C. but not exceeding 200° C. for 5 to 120 (preferably 30 to 120, more preferably from 40 to 100) minutes (or, according to an alternative preference, 5 to 20 minutes if the mixture is heated by superheated steam), wherein the polyalkenoic acid preferably has not more than 0.6 carboxylic acid groups per carbon atom in the backbone and is preferably poly(acrylic acid). The (ion-leachable) glass constituent of the cement preferably contains from 24 percent such as 32–60 (more preferably 32–45, such as 36–40) percent by weight silica.

The mixture is preferably allowed to set for from 5 to 15 minutes before the heating. If the maturing time is too short (e.g. 5 or 3 minutes or less), the samples could be damaged by being handled preparatory to the heating, and if it is too long (e.g. 3 hours), irreversible changes in the sample prevent the treatment according to the invention from having its full effect.

The duration of the heating may be from 20 to 120 minutes, such as 30 to 120 minutes, conveniently 40 to 60 minutes.

The duration of the heating and the temperature are preferably in any one of the following ranges:

75–100 minutes at 120° C.–140° C.; or

50–75 minutes at 140° C.–160° C.; or

40–50 minutes at 160° C.–180° C.; or with a low-silica glass and poly(acrylic acid), may be 20–40 minutes at 140° C.–160° C. The heating is preferably performed at a relative humidity of 100%, and need not be performed under a pressure exceeding 1½ atmospheres or even 1.01 atmospheres.

BRIEF DESCRIPTION OF THE DRAWINGS

The invention will now be described by way of example with reference to the accompanying drawing (FIG. 1), showing apparatus for treating glass ionomer cement samples according to the invention.

An open vessel 1 sits on a controllable hotplate 2 and contains silicone oil 3. In the vessel 1, supports 5 allow the oil 3 free access all round a stainless steel bomb 7 which is closed by a screw threaded lid 9 bearing lightly on an O-ring seal 10. The silicone oil 3 immerses the bomb to a depth of about 3 cm above the seal 10, and air and vapour inside the bomb at any pressure above about 1.005 atmospheres can escape into the oil 3 and bubble to the surface, but oil cannot enter the bomb 7.

In use, glass ionomer samples 20, which have been mixed, formed into shape while still workable (typically to form dental crowns), allowed to mature for 10 minutes after mixing and demoulded or removed from formers, are placed wet in the bomb 7, which is then lightly sealed. No special precautions are taken about the temperature or humidity of the air in the bomb but the wetness of the samples is sufficient for the relative humidity to attain 100% in the bomb.

The oil 3 has been preheated to the desired temperature (typically 130° C., 150° C. or 170° C.) and the bomb 7 is then placed in the vessel 1 and resting on the supports 5. It is found that the interior of the bomb reaches this temperature within about 1 minute. The bomb is maintained at this temperature for typically 30–90 minutes, after which the sample 20 is ready for permanent use.

After treatment in the bomb at the stated temperatures for the stated times, the following flexural strength results have been obtained from standard disc-shaped specimens, taking a mean of five samples. The glass used in the following list contained 38.8% $SiO_2$, 23.8% $Al_2O_3$, 5.2% $AlPO_4$, 5.2% $AlF_3$, 10.7% $CaF_2$, 11.1% NaF and 2.9% ZnO, and the acid was high molecular weight poly(acrylic acid) of molecular weight 50000 freshly dissolved to make a 50% solution in water. The powder/liquid ratio was 3:1.

| Temperature | Time | Flexural Strength |
|---|---|---|
| room temp | — | 43 MPa |
| 130° C. | 30 min | 38 MPa |
| 130° C. | 60 min | 47 MPa |
| 130° C. | 90 min | 87 MPa |
| 130° C. | 120 min | 56 MPa |
| 150° C. | 45 min | 52 MPa |
| 150° C. | 60 min | 88 MPa |
| 150° C. | 90 min | 55 MPa |
| 170° C. | 45 min | 82 MPa |
| 170° C. | 60 min | 62 MPa |
| 170° C. | 90 min | 78 MPa |
| 170° C. | 120 min | 43 MPa |
| 190° C. | 30 min | 32 MPa |
| 190° C. | 45 min | 70 MPa |
| 190° C. | 60 min | 80 MPa |
| 190° C. | 90 min | 58 MPa |

Results using a cement whose acid was as above but whose glass contained only 24% $SiO_2$ (and 14.3% $Al_2O_3$, 24.2% $AlPO_4$, 12.2% $AlF_3$, 12.8% $CaF_2$ and 11.5% NaF) were generally considerably inferior except for:

| Temperature | Time | Flexural Strength |
|---|---|---|
| 150° C. | 30 min | 88 MPa |

Results using cements whose glasses had 35–42% $SiO_2$ but whose polymeric acids contained half or all maleic acid units instead of solely acrylic acid units were unacceptable, typically with strengths less than half the above, at all times and temperatures.

All samples described performed satisfactorily in the erosion test, under a standard impinging jet of water, all scoring less than 0.01 mm loss per hour (some even scoring less than 0.002 mm/hr), the standard maximum permitted erosion loss being 0.05 mm/hour.

All samples had a reasonably smooth glassy gel exterior surface, as revealed by scanning electron micrography, and this is regarded as likely to be helpful in use in resisting staining, preventing microscopic-scale food particle entrapment and in eliminating crack nucleation sites.

In an alternative embodiment, the shaped glass ionomer samples matured for 10 minutes and then demoulded (all as previously described) are directly placed in a gas passage, wherein they are subjected to a jet of superheated steam at 120–200° C., e.g. 150° C. In this way, the samples extremely rapidly reach the desired temperature of at least 120° C., and a shorter exposure, namely 5 to 20 minutes (suitably 10 minutes) suffices to bring the tensile strength in favourable cases to above 100 MPa.

What is claimed is:

1. A method of treating an acid-base reaction cement, comprising heating an at least partly set shaped acid-base reaction mixture to above 120° C. but not exceeding 200° C. for 5 to 120 minutes.

2. A method according to claim 1, wherein the cement is a zinc-eugenol cement or a (dental silicate+phosphoric acid) cement.

3. A method according to claim 1, wherein the base is of acid-degradable glass.

4. A method according to claim 3, wherein the glass constituent of the cement is an ion-leachable glass containing at least 24% by weight silica.

5. A method according to claim 4, wherein the glass constituent of the cement is an ion-leachable glass containing 32–60% by weight silica.

6. A method according to claim 5, wherein the glass contains 32–45% by weight silica.

7. A method according to claim 3, wherein the cement is a glass polyalkenoate cement or a glass/polyphosphonate cement.

8. A method according to claim 7, wherein the polyalkenoic acid has not more than 0.6 carboxylic acid groups per carbon atom in the backbone.

9. A method according to claim 8, wherein the acid is poly(acrylic acid).

10. A method according to claim 1, wherein the heating is performed at a relative humidity of 100%.

11. A method according to claim 1, wherein the mixture has been allowed to set for from 5 to 15 minutes before the heating.

12. A method according to claim 1, wherein the heating is performed under a pressure not exceeding 1½ atmospheres.

13. A method according to claim 1, wherein the duration of the heating is from 20 to 120 minutes.

14. A method according to claim 1, wherein the duration of the heating is from 30 to 120 minutes.

15. A method according to claim 14, wherein the said duration is from 40 to 60 minutes.

16. A method according to claim 14, wherein the said duration is

75–100 minutes at 120° C.–140° C.; or

50–75 minutes at 140° C.–160° C.; or

40–50 minutes at 160° C.–180° C.

17. A method according to claim 4 wherein the duration of the heating is 20 to 40 minutes at a temperature of 140° C.–160° C.

18. A method according to claim 1, wherein the duration of the heating is from 5 to 20 minutes and wherein the mixture is heated by superheated steam.

* * * * *